United States Patent [19]

Watanabe et al.

[11] 4,330,526
[45] May 18, 1982

[54] SHAMPOO COMPOSITION

[75] Inventors: Hiroshi Watanabe, Funabashi; Tsuruo Mikata, Kashiwa; Kenichi Gohda, Saitama, all of Japan

[73] Assignee: Kao Soap Co., Ltd., Tokyo, Japan

[21] Appl. No.: 942,665

[22] Filed: Sep. 15, 1978

Related U.S. Application Data

[63] Continuation of Ser. No. 774,269, Mar. 4, 1977, abandoned.

[30] Foreign Application Priority Data

Mar. 22, 1976 [JP] Japan .................. 51-30996

[51] Int. Cl.³ .......................... A61K 7/06; C11D 3/48
[52] U.S. Cl. .................................... 424/70; 252/106
[58] Field of Search ............................. 424/70

[56] References Cited

U.S. PATENT DOCUMENTS

| | | | |
|---|---|---|---|
| 3,313,734 | 4/1967 | Lang et al. | 252/542 |
| 3,658,717 | 4/1972 | Graff | 252/547 X |
| 3,816,616 | 6/1974 | Anguillo et al. | 424/70 |
| 3,850,818 | 11/1974 | Katsumi et al. | 252/547 X |
| 3,962,418 | 6/1976 | Birkofer | 424/70 |
| 4,061,602 | 12/1977 | Oberstar et al. | 424/70 X |

OTHER PUBLICATIONS

Godfrey, K. M., "Cationic Emulsifiers in Cosmetics", J. Soc. Cosmetic Chemists, 17(1):1966, pp. 17–27.
McCutcheon, "Detergents and Emulsifiers 1971 Annual", 1971, pp. 6 and 48.

Primary Examiner—Dale R. Ore
Attorney, Agent, or Firm—Blanchard, Flynn, Thiel, Boutell & Tanis

[57] ABSTRACT

A hair shampoo composition comprising an anionic hairwashing surfactant, from 0.1 to 5.0 weight percent of a cationic surfactant having the formula

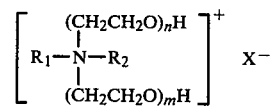

wherein $R_1$ is alkyl having 16 to 22 carbon atoms, $R_2$ is methyl, ethyl or alkyl having from 16 to 22 carbon atoms, x is halogen, methylsulfate or ethylsulfate, and m and n each is a number of at least one and the sum of m plus n is from 5 to 30, and from 0.1 to 3.0 weight percent of oleic acid monoglyceride.

4 Claims, No Drawings

SHAMPOO COMPOSITION

This is a continuation of application Ser. No. 774,269, filed Mar. 4, 1977, now abandoned.

BACKGROUND OF THE INVENTION

FIELD OF THE INVENTION

The present invention relates to a shampoo composition. More particularly, the present invention relates to a shampoo composition which can impart good suppleness and good smoothness to hair and improve the adaptability of hair to combing and brushing.

In general, when hair is washed with a hair shampoo, the sebum supplied from sebaceous glands is washed away, the touch or feel of the hair is worsened and it is difficult to run a comb through the washed hair. Especially, in the case of long hair of women, hairdressing is very difficult after washing.

In order to obviate this disadvantage, a hair rinsing agent comprising as the main component a cationic surface active agent having a long-chain alkyl group has heretofore been used for the treatment of hair previously washed with a shampoo. Such cationic surface active agent having a long-chain alkyl group is adsorbed on hair and, as is well known in the art, it exerts the effects of softening the touch or feel of hair and facilitating combing thereof. In general, the main component of a hair shampoo is an anionic surface active agent, and therefore, it is impossible to incorporate into a shampoo composition a cationic surface active agent of the type that is used in hair rinsing agents because the anionic and cationic surface active agents react with each other, resulting in the formation of precipitates. As a means for preventing this undesirable phenomenon, there has been proposed a shampoo for imparting a good finish to hair, in which an amphoteric surface active agent is used instead of the anionic surface active agent and it is combined with a cationic surface active agent (see, for example, Japanese Patent Publication No. 17363/73). However, amphoteric surface active agents are more expensive than anionic surface active agents and they are disadvantageous because they are inferior with respect to their washing power and foaming property. Therefore, such a shampoo has not yet been commercially marketed. It has been reported that a very special cationic surface active agent can be incorporated in a shampoo comprising as the basic ingredient an anionic surface active agent (see, for example, Japanese Patent Publication No. 47845/72).

In order to improve the touch or feel of hair washed with a shampoo, it has been attempted to incorporate an oily substance, such as liquid paraffin, into a shampoo comprising an anionic surface active agent as the basic ingredient. In this case, however, in order to prevent reduction of the principal properties of the shampoo, such as the foaming property and washing power, the amount of such oily substance contained in the shampoo must be limited and a satisfactory effect cannot be obtained.

SUMMARY OF THE INVENTION

We have studied various cationic surface active agents and various oils and fats with a view to developing a shampoo which can be manufactured at a low cost and which will exhibit the effects of improving the touch and feel, especially the suppleness and softness, of washed hair and facilitating combing or brushing of washed hair. We discovered that the combination of a cationic surface active agent having a specific chemical structure and a specific kind of an oily and fatty substance can be stably mixed with an anionic surface active agent so that a shampoo having a high hair touch-improving effect can be obtained.

More specifically, in accordance with the present invention, there is provided a shampoo composition comprising (A) an anionic surface active agent of the type customarily used in hair washing shampoos, (B) from 0.1 to 5.0% by weight, preferably 0.5 to 3.0% by weight, of a cationic surface active agent having the formula (I):

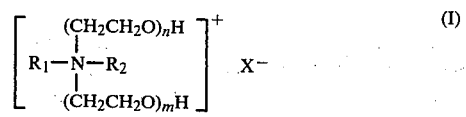

wherein $R_1$ is alkyl having 16 to 22 carbon atoms, $R_2$ is alkyl having 1 or 2 carbon atoms or alkyl having 16 to 22 carbon atoms, X is an anionic group selected from halogen and lower alkyl sulfate groups having 1 or 2 carbon atoms in the alkyl group, and m and n each is a number of at least one and the sum of n and m is in the range of from 5 to 30, and (C) from 0.1 to 3.0% by weight, preferably 0.3 to 1.0% by weight, of oleic acid monoglyceride (glyceryl monooleate).

Any of the anionic surface active agents customarily used as active detergent ingredients of hair shampoos can be used in the present invention. For example, there can be used alkali metal, ammonium and alkylol amine salts of alkyl ($C_{10}$ to $C_{16}$) sulfates, polyoxyethylene alkyl ($C_{10}$ to $C_{16}$) ether sulfates, alkyl ($C_{10}$ to $C_{16}$) sulfonates, alkyl ($C_{10}$ to $C_{16}$) benzene sulfonates and α-olefin ($C_{10}$ to $C_{16}$) sulfonates. The concentration of the anionic surface active agent is chosen so that an appropriate washing powder and foaming property can be attained. In general, the concentration of the anionic surface active agent is from 5 to 25% by weight, preferably 10 to 20% by weight.

The cationic surface active agent that is used in the present invention is prepared by adding ethylene oxide to an alkyl amine to form a tertiary amine and then quaternizing the tertiary amine with an alkyl halide or alkyl sulfate. If the number of moles of ethylene oxide added is smaller than 5, the compatibility of the resulting cationic surface agent with an anionic surface active agent is not good. If the number of added moles of ethylene oxide is larger than 30, the intended effects cannot be attained.

As the oily and fatty substance, oleic acid monoglyceride (glyceryl monooleate) is used in combination with the cationic surface active agent of formula (I), wherein there is attained a synergistic effect of improving the touch and feel of hair. When other oily and fatty substances, for example, fatty acids, higher alcohols, triglycerides and liquid paraffin are used, a satisfactory effect cannot be attained.

The shampoo composition may further comprise additives customarily incorporated into shampoos, for example, foaming boosters such as alkyl alkanolamides, dyes, perfumes and fungicides, present in the customary amounts.

The present invention will now be described in more detail by reference to Experiments illustrating the effects attained by incorporation of the cationic surface active agent and oleic acid monoglyceride and Examples illustrating specific embodiments of the shampoo composition of the present invention. In these Experiments and Examples, all references to "parts" and "%" are by weight.

| Experiment 1 | |
|---|---|
| Triethanolamine lauryl sulfate | 15.0% |
| Cationic surface active agent (various, see Table 1) | 1.0% |
| Deionized water | 84.0% |

Mixtures having the above composition were prepared by using various cationic surface active agents listed in Table 1 at room temperature. The compatibility of the various cationic surface active agents with triethanolamine lauryl sulfate were examined. The results obtained are shown in Table 1.

TABLE 1

| Sample No. | Cationic Surface Active Agent | Compatibility |
|---|---|---|
| 1 | $\left[\begin{array}{c} R\phantom{xx}CH_3 \\ \phantom{xx}N \\ R\phantom{xx}CH_3 \end{array}\right]^+ Cl^-$ | opaque, precipitated |
| 2 | $\left[\begin{array}{c} CH_3 \\ R-N-CH_3 \\ CH_3 \end{array}\right]^+ Cl^-$ | opaque, precipitated |
| 3 | $\left[\begin{array}{c} CH_3 \\ R-N-CH_2-C_6H_5 \\ CH_3 \end{array}\right]^+ Cl^-$ | opaque, precipitated |
| 4 | $\left[\begin{array}{cc} CH_3 & CH_3 \\ R-N-CH_2CH_2CH_2-N-CH_3 \\ CH_3 & CH_3 \end{array}\right]^{2+} 2Cl^-$ | substantially transparent |
| 5 | $\left[\begin{array}{c} (CH_2CH_2O)_nH \\ R-N-CH_3 \\ (CH_2CH_2O)_mH \end{array}\right]^+ Cl^-$ (m + n = 8) | transparent |
| 6 | $\left[\begin{array}{c} (CH_2CH_2O)_nH \\ R-N-R \\ (CH_3CH_2O)_mH \end{array}\right]^+ Cl^-$ (m + n = 25) | transparent |

Note
In Sample Nos. 1 to 6, R is alkyl having 16 to 18 carbon atoms.

Experiment 2

Compositions were prepared by adding 0.5% of an oily and fatty substance listed in Table 2 both alone, and together with 1.0% of the cationic surface active agent No. 5 used in Experiment 1, to an aqueous solution containing 15% of triethanolamine lauryl sulfate as an anionic surface active agent.

Human hair bundles having a length of 15 cm and a diameter of 2 cm were washed with the thus-prepared shampoo compositions, respectively, and the touch and feel of the hair after natural drying were examined and evaluated. More specifically, an unwashed hair bundle was compared with the washed hair bundle by a panel of 20 women with respect to the properties of touch and feel. Evaluation was made according to the following scale:
X: no substantial difference
Δ: washed hairs are slightly better than unwashed hairs
: washed hairs are better than unwashed hairs
: washed hairs are much better than unwashed hairs.

The results obtained are shown in Table 2.

TABLE 2

| | Effect of Improving Touch and Feel in Washed Hair | |
|---|---|---|
| Oily and Fatty Substance | only oil and fatty substance was incorporated | oily and fatty substance plus cationic surface active agent No. 5 were incorporated |
| liquid paraffin | Δ - X | Δ |
| isopropyl myristate | Δ | Δ |
| fatty acid ($C_{16}$-$C_{18}$) | X | X |
| higher alcohol ($C_{16}$-$C_{18}$) | X | X |
| triglyceride of $C_{16}$-$C_{18}$ fatty acids | Δ | Δ |
| oleic acid monoglyceride stearic acid monoglyceride | Δ | |

EXAMPLE 1

The following two shampoo compositions were prepared, and they were compared with each other with respect to the touch and feel of hair washed therewith.

| | Composition (A) (present invention) | Composition (B) (comparison) |
|---|---|---|
| Triethanolamine lauryl sulfate | 15.0% | 15.0% |
| Lauryl diethanolamide | 3.0% | 3.0% |
| EDTA-2Na | 0.3% | 0.3% |
| $\left[\begin{array}{c} (CH_2CH_2O)_nH \\ R-N-CH_3 \\ (CH_2CH_2O)_mH \end{array}\right]^+ Cl^-$ (R is alkyl having 18 carbon atoms) (n + m = 8) | 1.0% | zero |
| Oleic acid monoglyceride | 0.5% | zero |
| Perfume | minute amount | minute amount |
| Dye | minute amount | minute amount |
| Deionized water | balance | balance |
| Total | 100% | 100% |

Two hair tresses (human hairs were gathered to form a bundle having a length of about 15 cm and a diameter of about 2 cm and the root ends were bonded with an adhesive) were washed with the above shampoos (A) and (B), respectively, and the tresses were drained of water and they were compared with each other with respect to their touch and feel by a panel of 20 women while they were still in the wet state. The results obtained are shown in Table 3.

TABLE 3

| Answer | Number of Persons |
|---|---|
| (A) is better than (B) | 15 |
| No substantial difference | 3 |

TABLE 3-continued

| Answer | Number of Persons |
|---|---|
| (B) is better than (A) | 2 |

From the above results, it will readily be understood that the shampoo (A) according to the present invention is superior to the comparative shampoo (B) with respect to the finishing effect.

Example 2

| Sodium polyoxyethylene lauryl ether sulfate | 14.0% |
|---|---|
| Sodium lauryl sulfate | 2.0% |
| Lauryl diethanolamide | 2.0% |
| EDTA-2Na | 0.3% |
| $\left[\begin{array}{c}(CH_2CH_2O)_nH\\ \vert\\ R-N-CH_3\\ \vert\\ (CH_2CH_2O)_mH\end{array}\right]^+ Cl^-$ (R is alkyl having 18 carbon atoms) (n + m = 10) | 1.0% |
| Oleic acid monoglyceride | 0.6% |
| Perfume and dye | minute amounts |
| Deionized water | balance |
| Total | 100% |

A shampoo of the present invention having the above composition exhibited a good finishing effect when used for washing hair and imparted a good touch and feel to the hair.

Example 3

| Diethanolamine lauryl sulfate | 20.0% |
|---|---|
| Lauryl diethanolamide | 3.0% |
| $\left[\begin{array}{c}(CH_2CH_2O)_nH\\ \vert\\ R-N-CH_3\\ \vert\\ (CH_2CH_2O)_mH\end{array}\right]^+ Cl^-$ (R is alkyl having 20 to 22 carbon atoms) (n + m = 20) | 0.8% |
| Oleic acid monoglyceride | 0.4% |
| Dye | minute amount |
| Perfume | minute amount |
| Deionized water | balance |
| Total | 100% |

When hair was washed with a shampoo of the present invention having the above composition, the shampoo exhibited a good finishing effect to the washed hair and imparted a good touch and feel to the washed hair.

The embodiment of the invention in which an exclusive property or privilege is claimed are defined as follows:

1. A liquid shampoo composition consisting essentially of from 5 to 25% by weight of a water-soluble, synthetic, organic, anionic surface active agent effective for shampooing hair selected from the group consisting of alkali metal, ammonium and alkylol amine salts of alkyl sulfates, alkyl ether sulfates, alkyl sulfonates, alkyl benzene sulfonates and α-olefin sulfonates, from 0.1 to 5.0% by weight of a cationic surface active agent having the formula (I):

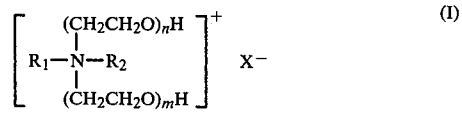

wherein $R_1$ is alkyl having 16 to 22 carbon atoms, $R_2$ is methyl, ethyl or alkyl having 16 to 22 carbon atoms, X is halogen, methyl sulfate or ethyl sulfate, and m and n each is a number of at least one and the sum of n and m is in the range of from 5 to 30, from 0.1 to 3.0% by weight of oleic acid monoglyceride, and the balance is essentially water.

2. A shampoo composition as set forth in claim 1 wherein the amount of the anionic surface active agent is from 10 to 20% by weight, the amount of the cationic surface active agent is from 0.5 to 3.0% by weight and the amount of said oleic acid monoglyceride is 0.3 to 1.0% by weight.

3. A shampoo composition as set forth in claim 1 wherein $R_1$ is stearyl and $R_2$ is methyl.

4. A shampoo composition as set forth in claim 3 wherein the anionic surface active agent is triethanolamine lauryl sulfate.

* * * * *